United States Patent [19]

Messner et al.

[11] Patent Number: 4,875,489
[45] Date of Patent: Oct. 24, 1989

[54] EXTENDABLE GUIDEWIRE

[75] Inventors: Kirsten L. Messner, Belmont; Robert M. Abrahms, Mountain View; Ray R. Beitelia, Santa Clara, all of Calif.

[73] Assignee: Advanced Cardiovascular Systems, Inc., Mountain View, Calif.

[21] Appl. No.: 86,102

[22] Filed: Aug. 14, 1987

[51] Int. Cl.$^4$ .............................................. A61B 5/00
[52] U.S. Cl. .................................. 128/772; 128/657; 604/164; 604/283
[58] Field of Search ............... 128/343, 344, 657, 658, 128/772; 604/95, 164, 166, 170, 171, 283, 905; 403/109, 221, 222, 297, 334

[56] References Cited

U.S. PATENT DOCUMENTS

| 4,239,042 | 12/1980 | Asai | 604/164 |
|---|---|---|---|
| 4,299,228 | 11/1981 | Peter | 128/772 |
| 4,419,025 | 12/1983 | Takahashi | 403/109 |
| 4,451,256 | 5/1984 | Weikl et al. | 128/343 |
| 4,538,622 | 9/1985 | Samson et al. | 128/772 |
| 4,547,194 | 10/1985 | Moorehead | 604/283 |
| 4,569,347 | 2/1986 | Frisbie | 128/344 |
| 4,702,252 | 10/1987 | Brooks et al. | 128/344 |

FOREIGN PATENT DOCUMENTS

| 113314 | 3/1969 | Denmark | 604/164 |
|---|---|---|---|
| 3444232 | 6/1986 | Fed. Rep. of Germany | 128/343 |

Primary Examiner—Max Hindenburg
Attorney, Agent, or Firm—Fulwider, Patton, Rieber, Lee & Utecht

[57] ABSTRACT

An extendable guidewire for introducing a dilatation catheter into the cardiovascular system. The guidewire has main and auxiliary sections with a connector which permits the two sections to be joined together and separated simply by pushing the two sections together and pulling them apart. One of the sections can be used for positioning the catheter within the cardiovasuclar system, and the other section can be employed to extend the wire to change catheters.

5 Claims, 1 Drawing Sheet

EXTENDABLE GUIDEWIRE

BACKGROUND OF THE INVENTION

This invention pertains generally to cardiovascular procedures such as angioplsaty, angiography and valvuloplasaty, and more particularly to an extendable guidewire and the methods of manufacturing and using the same.

Guide wires are currently used to facilitate the placement of dilatation catheters in the arterial system of a patent for cardiovascular procedures such as angioplasty, angiography and valvuloplasty. The guidewire is typically on the order of 20-50 cm longer thana the catheter to permit the guidewire and the catheter to be advanced relative to each other as they are steered into position within the patient's body. Suitable guidewires are described in U.S. Pat. No. 4,538,622 (Samson et al.) and U.S. Pat. No. 4,569,347 (Frisbie) which are hereby incorporated herein in their entirety.

In the usual procedure to change dilatation catheters, the guidewire is removed from the patient, and an exchange wire is inserted in its place. The exchange wire is substantially longer than the guidewire, and it generally extends outside the patient's body for a distance greater than the length of the catheter. With a dilation catheter having a length on the order of 120-140 cm, for example, a guidewire might have a length on the order of 175 cm, and an exchange wire might have a length on the order of 300 cm. The use of an exchange wire has the obvious disadvantage that it adds extra steps to the angioplasty procedures. In addition, it requires the doctor to have an additional wire for this purpose.

Heretofore, there have been some attempts to eliminate the need for a separate exchange wire by attaching an extension wire to a coronary wire to extend the length of the wire. The two wires are joined together by a crimped connector which requires a special tool. Once the connector has been crimped, the connection is permanent, and the extension wire cannot be removed except by cutting it loose from the coronary wire.

What has been needed and heretofore unavailable is an extension which can be readily connected and disconnected to the guide wire and when in position withiin the patient. The present invention satisfies this need.

SUMMARY OF THE INVENTION

It is in general an object of the invention to provide a new and improved guidewire and methods of manufacturing and using the same.

Another object of the invention is to provide a guidewire and methods of the above character in which the guidewire can be extended in length and readily returned to its original length.

These and other objects are achieved in accordance with the invention by providing a guidewire having main and auxiliary sections which are detachably secured together by press fitting. One of the wire sections has an expandable tubular portion at the connecting end thereof, and the second wire section has a end portion tion to expand the portion and to be gripped thereby to detachably securing the two sections together. The two sections can be readily separated by pulling them apart. The two sections can be reconnected and disconnected as many times as desired.

In a presently preferred embodiment the expandable portion is cylindrically shaped with a longitudinally split which is adapated to receive the connecting end at the second wire section. The connecting end of the second wire section is preferably tapered slightly to facilitate the insertion thereof into the split tubular cylindrically shaped expandable portion.

DETAILED DESCRIPTION OF THE INVENTIONS

Figure 1:
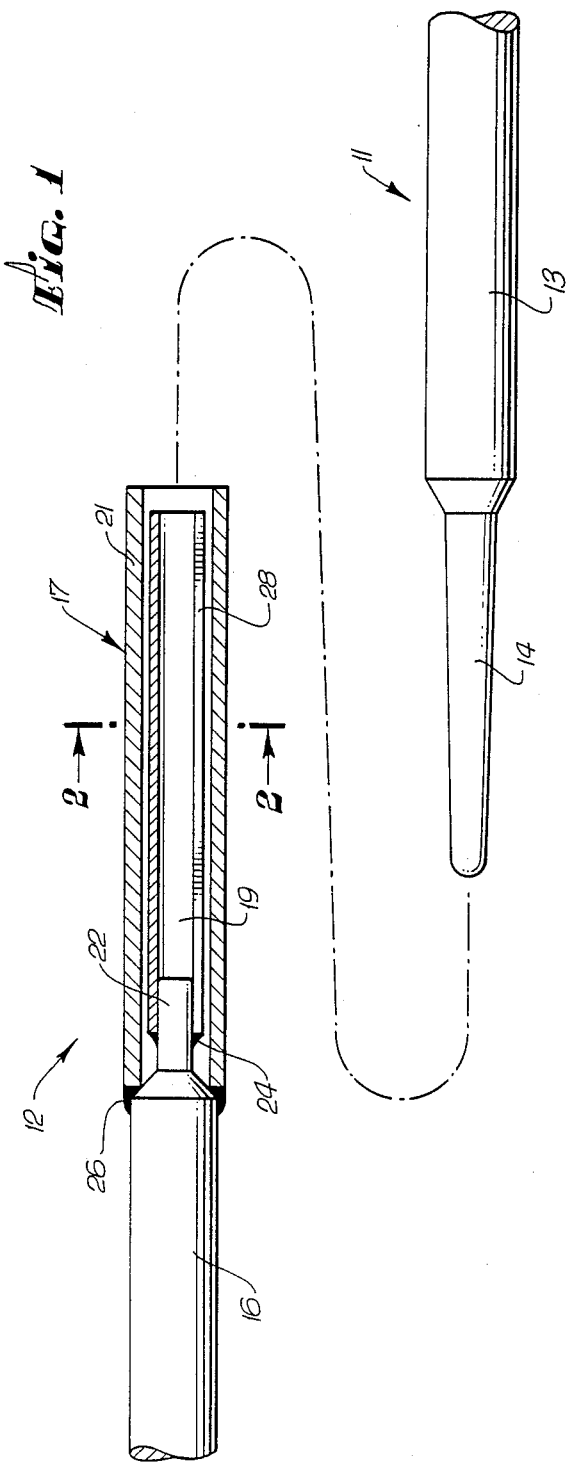
FIG. 1 is a fragmentary centerline sectional view of an embodiment of an extendable guidewire according to the invention.
Figure 2:
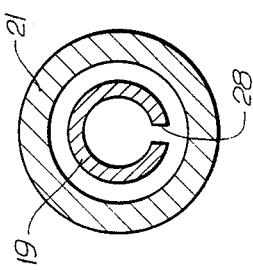
FIG. 2 is a cross-sectional view taken along line 2—2 in FIG. 1.

As illustrated in the drawings, the guidewire has a main section 11 which is adapted to be inserted into the patient's vascular system and an auxiliary section 12 which can be connected and disconnected to the proximal end of the main section. Section 11 has an elongated shaft 13 with a flexible tip (not shown) at its distal end and a tapered portion 14 at its proximal end. Details of of this structure can be found in the references cited previously and incorporate herein by reference thereto. Section 12 also has an elongated shaft 1 with a connector 17 at its distal end for mating engagement with the tapered portion at the proximal end of Section 11. The guidewire is intended for use in positioning a dilatation catheter (not shown) in the cardiovascular system of a patient, and section 11 has a length corresponding to the length of a conventional guidewire for this purpose. Details of typical dilatation catheters can be found in the references cited previously and incorporated herein.

Section 12 has a length such that when the two sections are connected together the wire has an overall length suitable for exchanging catheters without removing section 11 from the patient's body. With a dilatation catheter having a length on the order of 120-140 cm, for example, section 11 might have a length on the order of 140-175 cm, and section 12 might have a length on the order of 125-160 cm.

Shafts 13, 16 can be fabricated from any suitable material such as stainless steel, and neach should have a diameter such that a dilatation catheter can pass freely over them. Although two shafts 13 and 16 do not have to have exactly the same diameter, it is preferably that the two shafts be of substantially the same diameter in order to provide a smooth transition between them. In one presently preferred embodiment for use in coronary angioplasty, shaft 13 has a diameter on the order of 0.013-0.016 inch, and shaft 16 has a diameter of 0.014 inch. Either or both of the shafts can be provided with a coating of Teflon or another suitable low friction material to facilitate movement of the catheter over the wire.

Connector 17 comprises an inner tubular member 19 and an outer tubular ember or sleeve 21. Tubular member 19 is mounted on a short axial extensionn 22 of reduced diameter at the distal end of shaft 16. The distal end portion of this tubular member fits over the post and is affixed thereto by suitable means such as an adhesive or soldering or welding, as indicated at 24. Post 22 can be formed by any suitable means such as grinding down the proximal end portion of the shaft.

Sleeve 21 is positioned co-axially of tubular member 19 and affixed to shaft 16 near the base of post 22 by suitable means such as soldering or welding 26. Tubular member 19 and sleeve 21 are each fabricated of a suitable material such as stainless steel.

Tubular member 19 has a longitudinally extending split or slot 28 which permits the tubular member to expand as the tapered end portion 14 of wire section is inserted into the tubular member. Sleeve 21 limits the amountn the tubular member can expand and adds overall strength and rigidity to the connection. In one presently preferred embodiment, tubular member 19 is fabricated or stainless steel tubing have a longitudinally extending welded seam, and slot 28 is formed by pressing a mandrel into the tubing to split the seam. Alternatively, the slot can be formed by other means such as cutting with a millting cutter or with a laser.

The distal end of the tapered end portion 14 of wire section 11 should have a diameter slightly less than the unexpanded inside diameter of tubular member 19 and the distal end or base of the tapered portion should have a somewhat greater diameter than the unexpanded tubular member to ensure proper connection. In a guidewire having a diameter on the order of 0.014 inch, for example, tubular member 19 might have an unexpanded inner diameter on the order of 0.007 inch and a wall thickness on the ordre of 0.001 inch, sleeve 21 might have an inner diameter on the order of 0.012 inich and a wall thickness of 0.0015 inch, and tapered end portion 14 might have a linear taper on the order of 1.7–1.8 cm in length with a diameter on the order of 0.0085 inch midway along this length. In this embodiment, sleeve 21 might have a length on the order of 2.4–2.5 cm.

The guidewire and the expansion can be manufactured by grinding the proximal and distal end portions of shafts 13 and 16 to form tapered portion 14 and post ground as desired and provided with a spring coil (not shown) to form a flexible tip for the wire. Tubular member 19 is placed on post 22 and soldered or otherwise bonded in position, and outer tubular member or sleeve 21 is positioned over the inner tubular member and soldered or otherwise bonded to the shaft. Slot 28 can be formed either before or after tubular member 19 is attached to the shaft. In one presently preferred embodiment, it is formed by pressing a tapered mandrel into the tube to split it longitudinally. Alternatively, the slot can be formed by cutting with a milling cutter or with a laser as previously discussed.

In use, section 11 of the guidewire is introduced into the vascular system of a patient with a dilatation catheter through a guiding catheter and an introducer. When performing a coronary angioplasaaty the guiding catheter is positioned in the coronary ostium, and the dilatation catheter is advancaed so that it is just proximal to the tip of the guiding cathether.

The tip of the guidewire is advanced beyond the distal tip of the dilatation catheter while holding the dilatation catheter in place. As the guidewire is advanced, it is rotated and steered into the selected artery. The guidewire tip is preferably advanced through the lesion and beyond it, if possible. This permits the balloon portion of the catheter to be positioned over a more supportive section of the guidewire within the lesion. Once the guidewire is in position, it is held in place and the dilatation catheter is advanced alongit until the inflatable balloon thereof is within the lesion. Tapered end portion 14 remains outside the patient's body and outside any adapter which may be connected to the proximal end of the dilatation cathether.

To exchange catheters, the guidewire is extended by manually pressing together the tubular inner member 19 of connection 17 or the distal end of 16 and the tapered section 11 in the patient's body. As the tapered end portion 14 is inserted into the tubular member 19, the tubular member expands, and the resiliency of the expanded tubular member causes it to grip the tapered portion to firmly hold the two sections together. The dilatation catheter can then be withdrawn from the patient's body over the extended guidewire.

A new dilatation catheter can then be introduced over section 12 and advanced along the wire setion 11 within the patient's body until the balloon crosses the lesion. Once the proximal end portion of the new balloon has advanced beyond connector 17 and tapered end portion 14, section 12 can be removed by grasping the two sections of the wire on opposite sides of the connector 17 and pulling them apart without disturbing the position of section 11 in the patient's body.

The main and auxiliary sections 11 and 12 of the guide can be connected together and disconnected as many times as necessary simply by prssing them together and pulling them apart.

The invention has a number of important features and advantages. The two sections of the wire can be connected together whenever a longer wire is needed, and they can be separated wheneer the additional length is not required. The two sections of the wire are connected and disconnected by simply pressing them together and pulling them apart. This can be done as many times as necessary, and no special tools are required either to make the connection or to separate it.

It is apparent from the foregoing that a new and improved extended guidewire and methods of manufacturing and using the same have been provided. While only certain presently preferred embodiments have been described in detail, as will be apparent to those familiar with the art, certain changes and modifications can be made without departing from the scope of the invention as defined by the following claims.

What is claimed is:

1. An extendable guidewire system adapted for use within a patient's vasculature comprising:
   a first guidewire section having secured at one end thereof an expandable inner tubular portion with a longitudinal slot therein and an outer tubular member surrounding the inner tubular portion which restricts the expansion of the inner member; and
   a second guidewire section having a male end portion which is adapted to be inserted into the tubular portion of the first guidewire section with the longitudinal slot therein to expand the slotted tubular portion and which has a diametrical dimension larger than the diameter of the slotted tubular member and thereby detachably securing the two wire sections together.

2. The extendable guidewire of claim 1 wherein the first guidewire section includes an axial extension of reduced cross-sectional area, the expandable tubular portion mounted on the axial extension and extending axially therefrom, and an outer tubular member secured to the first guidewire section adjacent to the extension and having substantially the same diameter as the first guidewire section.

3. The extendable guidewire of claim 2 wherein the outer tubular member is disposed co-axially about the inner tubular portion and limits the expansion of the inner tubular portion.

4. The extendable guidewire of claim 1 wherein the male end portion of the second guidewire section is tapered so that the tip thereof is smaller in diameter than the diameter of the tubular portion with a longitudinal slot to facilitate the entry of the male end portion therein.

5. A method of using an extendable guidewire in a cardiovascular procedure, said guidewire having a pair of axially elongated sections with connector parts at the mating ends thereof, one of said connector parts comprising a longitudinally split peripherally expandable tubular member and the other of said connector parts comprising a tapered portion at the end of the section, the steps of:

introducing a first one of the wire sections into the cardiovascular system of a patient with the connector part of that wire section remaining outside the body of the patient;

advancing a first catheter along the wire section within the cardiovascular system;

detachably connecting the second wire section to the first wire section by manually pressing the tapered end portion into the tubular member to expand the tubular member so that it grips the tapered end portion without removing the first wire section from the cardiovascular system, withdrawing the first catheter from the cardiovascular over the first and second guidewire sections, introducing a second catheter into the cardiovascular system over the two wire sections; and removing the second section by manually pulling the two wire sections apart to disengage the tapered end portion from the tubular member with the first wire section remaining in place in the cardiovscular system.

* * * * *

UNITED STATES PATENT AND TRADEMARK OFFICE
CERTIFICATE OF CORRECTION

PATENT NO. : 4,875,489
DATED : October 24, 1989
INVENTOR(S) : Kirsten L. Messner et al It is certified that error appears in the above-identified patent and that said Letters Patent is hereby corrected as shown below:

```
Column 1, line 14, "thana" should be --than--
          line 44, "withiin" should be --within-- line 25, "1" should be --16--
          line 43, "neach" should be --each--
          line 46, "preferably" should be --preferable--
          line 59, "extensionn" should be --extension--
Column 3, line 7,  "amountn" should be --amount--
          line 14  "millting" should be --milling--
          line 24  "ordre" should be --order--
          line 25  "inich" should be --inch--
          line 49  "angioplasaaty" should be --angioplasty--

Column 4, line 20  "pissing" should be --pressing--
          line 25, "wheneer" should be --whenever--
Claim 2, line 3, after "expandable" and before "tubular"
          insert the word --inner--.
```

Signed and Sealed this

Twenty-eighth Day of January, 1992

Attest:

HARRY F. MANBECK, JR.

*Attesting Officer*       *Commissioner of Patents and Trademarks*